(12) United States Patent
Scrantz et al.

(10) Patent No.: US 10,179,050 B2
(45) Date of Patent: Jan. 15, 2019

(54) ENCEPHALOCELE REPAIR DEVICE

(71) Applicants: Kelly J. Scrantz, Baton Rouge, LA (US); Bret Michael Berry, Tallahassee, FL (US)

(72) Inventors: Kelly J. Scrantz, Baton Rouge, LA (US); Bret Michael Berry, Tallahassee, FL (US)

( * ) Notice: Subject to any disclaimer, the term of this patent is extended or adjusted under 35 U.S.C. 154(b) by 204 days.

(21) Appl. No.: 14/860,283

(22) Filed: Sep. 21, 2015

(65) Prior Publication Data

US 2017/0079705 A1 Mar. 23, 2017

(51) Int. Cl.
*A61F 2/28* (2006.01)
*A61B 17/68* (2006.01)
*A61F 2/30* (2006.01)
*A61B 17/88* (2006.01)

(52) U.S. Cl.
CPC ............ *A61F 2/2875* (2013.01); *A61B 17/68* (2013.01); *A61B 17/8872* (2013.01); *A61F 2002/30561* (2013.01); *A61F 2250/0025* (2013.01); *A61F 2250/0036* (2013.01); *A61F 2250/0098* (2013.01)

(58) Field of Classification Search
CPC .................. A61F 2/0063; A61F 2/2875; A61F 2002/2878; A61F 2002/2882; A61F 2002/2885; A61F 2002/2889; A61F 2/0009; A61B 17/8872
See application file for complete search history.

(56) References Cited

U.S. PATENT DOCUMENTS

| | | | | |
|---|---|---|---|---|
| 2006/0224242 A1* | 10/2006 | Swords | .............. | A61B 17/8085 623/17.19 |
| 2007/0270841 A1* | 11/2007 | Badie | ................. | A61B 17/8061 606/86 A |
| 2010/0312284 A1* | 12/2010 | Linares | .............. | A61B 17/8061 606/286 |
| 2011/0087232 A1* | 4/2011 | Levatich | ............ | A61B 17/8811 606/94 |
| 2014/0172014 A1* | 6/2014 | Fitzgerald | .......... | A61B 17/0057 606/213 |

OTHER PUBLICATIONS

Medical Tools "Weil-Blakesley Nasal Cutting Forceps Fig 5" http://www.medical-tools.com/shop/weil-blakesley-nasal-cutting-forceps-fig-5.html. Accessed Jun. 7, 2018.*

* cited by examiner

*Primary Examiner* — Carrie R Dorna
(74) *Attorney, Agent, or Firm* — James M. Smedley LLC; James Michael Smedley, Esq.

(57) ABSTRACT

The present invention generally relates to a device for repairing an encephalocele. Specifically, this invention relates to a patching component that can be implanted or grafted on to the skull to repair an encephalocele from the inner or outer surface of the skull.

13 Claims, 4 Drawing Sheets

ENCEPHALOCELE REPAIR DEVICE

FIELD OF THE INVENTION

The present invention generally relates to a device for repairing an encephalocele. Specifically, this invention relates to a patching component that can be implanted or grafted on to the skull to repair an encephalocele from either the inner or the outer surface of the skull.

BACKGROUND OF THE INVENTION

An encephalocele can be generally described as a hole or similar injury to the skull where the brain and brain lining herniate out from the interior of the skull to the exterior of the skull through such hole or other injury. This defect can result from a variety of factors, including congenital causes, tumors, infections, and other traumas to the skull where the cranial vault is compromised causing the brain and brain lining to push out from the interior of the skull.

There are two primary methods for repairing an encephalocele. The first method involves repairing the encephalocele using a patch that is grafted to the outside of the skull. The second method involves repairing the encephalocele by using a patch that is grafted on the inside of the skull. In general, as the size of the hole increases, the more likely it is that the encephalocele will need to be repaired using the inside repair method. However, many of the currently available encephalocele patches and patch construction techniques have a number of drawbacks. For example, to repair larger encephaloceles with the inside repair method typically requires using a rigid material such as bone or metal that is adequately firm to prevent the graft from herniating back through the hole in the skull. Bone and metal grafts have a number of drawbacks that make those materials difficult to work with. In particular, bone is difficult to work with because it first must be transplanted from another area of the skull and then shaped down to fit the encephalocele. Likewise, metal has its own problems including edges that can catch on other materials used in the graft and metal creates artifacts on imaging which make observation of the graft difficult.

Therefore, there is a need in the art for an encephalocele repair device that can be easily adapted to treat encephaloceles of varying size and is substantially radiolucent. These and other features and advantages of the present invention will be explained and will become obvious to one skilled in the art through the summary of the invention that follows.

SUMMARY OF THE INVENTION

Accordingly, embodiments of the present invention are directed to a radiolucent encephalocele repair device that can be adapted to repair encephaloceles of varying diameters and sizes. Embodiments of the present invention may include an insertion push rod that is used to implant the encephalocele repair device on the inside of the skull from the outside of the skull without a separate access point being cut into the skull.

According to an embodiment of the present invention, an encephalocele repair device comprising: an encephalocele patching component comprising a wall of material formed with a convex front side and a concave rear side and a patching component insertion rod configured to engage with and apply pressure to said concave rear side of said encephalocele patching component during deployment of said encephalocele patching component.

According to an embodiment of the present invention, the encephalocele patching component varies in thickness between 0.5 mm and 3.5 mm.

According to an embodiment of the present invention, the encephalocele patching component decreases in thickness as said wall of material radiates outward from a center point of said encephalocele patching component.

According to an embodiment of the present invention, the encephalocele patching component increases in thickness as said wall of material radiates outward from a center point of said encephalocele patching component.

According to an embodiment of the present invention, the encephalocele patching component has a diameter between 0.5 cm and 3.5 cm.

According to an embodiment of the present invention, the encephalocele patching component is further comprised of one or more radiopaque markers secured to said encephalocele patching component.

According to an embodiment of the present invention, the encephalocele patching component is further comprised of a grafting surface area formed on said concave rear side, wherein said grafting surface area is a textured surface that promotes grafting between said encephalocele repair device and body tissue.

According to an embodiment of the present invention, the grafting surface area is a strip of textured surface bordering said concave rear surface on one or more perimeter edges.

According to an embodiment of the present invention, the patching component insertion rod is attached to said encephalocele patching component via an adaptable connection comprising a rod attachment point on said concave rear side of said encephalocele patching component and a patching component attachment point on said patching component insertion rod.

According to an embodiment of the present invention, the encephalocele repair device comprising: an encephalocele patching component comprising a wall of material formed with a convex front side, a concave rear side, and a grafting surface area formed on said concave rear side that promotes grafting between said encephalocele repair device and body tissue.

According to an embodiment of the present invention, the encephalocele patching component is further comprised of a patching component insertion rod configured to engage with and apply pressure to said concave rear side of said encephalocele patching component during deployment of said encephalocele patching component.

According to an embodiment of the present invention, the patching component insertion rod is attached to said encephalocele patching component via an adaptable connection comprising a rod attachment point on said concave rear side of said encephalocele patching component and a patching component attachment point on said patching component insertion rod.

According to an embodiment of the present invention, the encephalocele patching component is further comprised of one or more radiopaque markers secured to said encephalocele patching component According to an embodiment of the present invention, the grafting surface area is a strip of textured surface bordering said concave rear surface on one or more perimeter edges.

According to an embodiment of the present invention, the encephalocele patching component has a variable thickness to enable a variable flexibility across said encephalocele patching component.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

DETAILED SPECIFICATION

Figure 1:
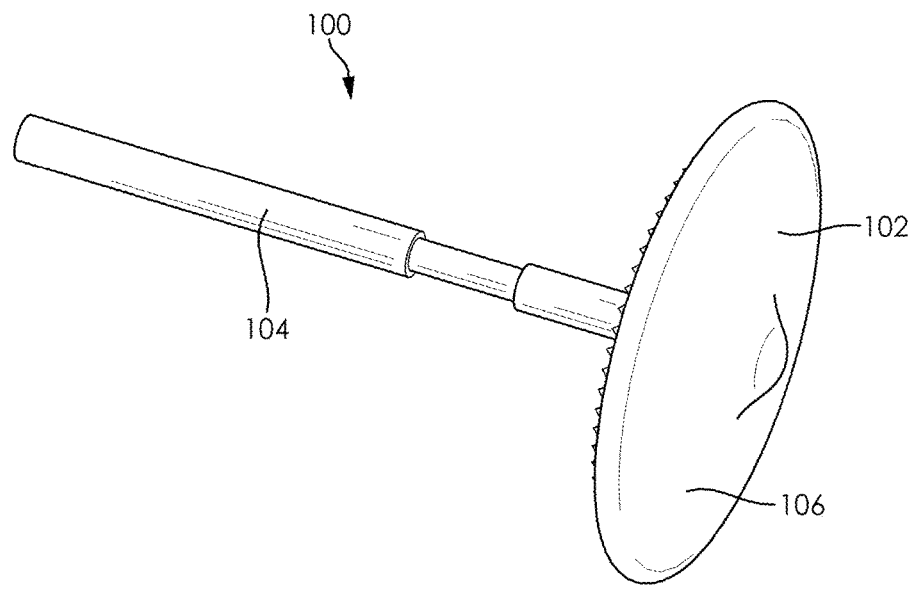
FIG. 1 is a perspective view of encephalocele repair device in accordance with an embodiment of the present invention.

The present invention generally relates to a device for repairing an encephalocele. Specifically, this invention relates to a patching component that can be implanted or grafted on to the skull to repair an encephalocele from the inner or outer surface of the skull.

According to an embodiment of the present invention, an encephalocele repair device is comprised of an encephalocele patching component and a patching component insertion rod. Additional components may include, but are not limited to, a grafting surface area formed on the encephalocele patching component, an adaptable connection formed between the encephalocele patching component and the patching component insertion rod, and one or more radiopaque markers secured to the encephalocele patching component. Some embodiments of the present invention may include fewer or additional components depending on the specific application of the encephalocele repair device. For example, in some embodiments, the encephalocele repair device may be primarily comprised of the encephalocele patching component and omit the patching component insertion rod. One of ordinary skill in the art would appreciate that there are many possible configurations and components for an encephalocele repair device, and embodiments of the present invention are contemplated for use with any such configuration or component.

According to an embodiment of the present invention, the encephalocele repair device is constructed from any variety of suitable durable materials. In a preferred embodiment, the majority of the encephalocele repair device is comprised of any radiolucent material that is suitable for use inside the human body. A primary example of such a radiolucent material is polyether ether ketone (PEEK), but one of ordinary skill in the art would appreciate that there many radiolucent materials that would suitable for producing an encephalocele repair device. In some embodiments, the encephalocele repair device may include certain radiopaque materials so that the encephalocele patching component remains visible to x-rays and other imaging technologies. One of ordinary skill the art would appreciate that there are numerous suitable materials from which the components of the encephalocele repair device could be manufactured, and embodiments of the present invention are contemplated for use with any such material.

According to an embodiment of the present invention, the encephalocele repair device is comprised of an encephalocele patching component. In a preferred embodiment, the encephalocele patching component (also referred to as the patching implant or implant) is comprised a curved wall forming a convex front side and a concave rear side. In the preferred embodiment, the encephalocele patching component is disk-shaped with a circumference between 0.5 cm and 3.5 cm and a thickness between 0.5 mm and 3.5 mm. It would be understood by one of ordinary skill in the art the shape and size ranges of the encephalocele patching component could be varied with departing from spirit and scope of the invention. In the preferred embodiment, the patching implant may vary in thickness across the length and width of the implant. In some embodiments, the patching implant may generally decrease in thickness from the center of the implant to the edges of the implant, creating a patching implant that is more rigid in the middle than at the edges. In some embodiments, the patching implant may generally increase in thickness from the center of the implant to the edges of the implant, creating a patching implant that is more flexible in the middle than at the edges. One of ordinary skill in the art would appreciate that there are many suitable designs for an encephalocele patching component, and embodiments of the present invention are contemplated for use with any such design.

According to an embodiment of the present invention, the encephalocele patching component is comprised of a convex front side. In a preferred embodiment, the convex front side is domed shape to provide support to the encephalocele. In the preferred embodiment, the convex front side of the encephalocele patching component has a substantially smooth surface. One of ordinary skill in the art would appreciate that the convex front side of the encephalocele patching component could be formed with varying degrees of curvature, and embodiments of the present invention are contemplated for use with any such degree of curvature.

According to an embodiment of the present invention, the encephalocele patching component is comprised of a concave rear side. In a preferred embodiment, the concave rear side is further configured with a grafting surface area. In some embodiments, the concave rear side may also be configured with a rod attachment point. One of ordinary skill in the art would appreciate that there are many suitable configurations for the concave rear side of the encephalocele patching component, and embodiments of the present invention are contemplated for use with any such configuration.

According to an embodiment of the present invention, the concave rear side may be further configured with a grafting surface area. In a preferred embodiment, the grafting surface area is a textured surface formed on at least a portion of the concave rear side. In the preferred embodiment, the grafting surface area forms a textured strip at the edge of the concave rear side. The texturing on the grafting surface area may include, but is not limited to, ridges, grooves, holes, dimpling, or a raised diamond pattern. In the preferred embodiment, the grafting surface area promotes grafting between the encephalocele patching component and the body tissue where the patching implant is positioned and should eventually lead to the encephalocele repair device being secured into place by scar tissue. In some embodiments, the grafting surface area may cover substantially more of the concave rear side than just a strip at the edge of the concave rear side. One of ordinary skill in the art would appreciate that there are many possible configurations and textures that could be used for a grafting surface area, and embodiments of the present invention are contemplated for use with any such configuration or texture.

According to an embodiment of the present invention, the encephalocele repair device is comprised of a patching component insertion rod. In a preferred embodiment, the patching component insertion rod (or insertion rod) is a generally cylindrical shaft configured to facilitate the implantation of the encephalocele patching component at the encephalocele repair site on the skull of a patient. In the preferred embodiment, the insertion rod and may be further configured with a patching component attachment point at one of the insertion rod. The patching component attachment point may be configured to correspond to a rod attachment point on the encephalocele patching component, which collectively would form the adaptable connection. In the preferred embodiment, the insertion rod may have a variable diameter. In some embodiments, the insertion rod may have a constant diameter. One of ordinary skill in the art would appreciate that there are many suitable designs for a patching component insertion rod, and embodiments of the present invention are contemplated for use with any such design According to an embodiment of the present invention, the encephalocele repair device is comprised of an adaptable connection. In a preferred embodiment, the adaptable connection is formed by the rod attachment point on the concave rear side of the encephalocele patching component and the patching component attachment point on the insertion rod. In the preferred embodiment, the adaptable connection may feature a detachable connection so that the insertion rod can be removed from the patching implant. This would be facilitated by an adaptable connection that was rigid enough to allow for the implantation of the patching implant, but not so robust to make separation overly difficult. For example, the adjustable connection should be easily severable by any common surgical cutting tool. In an alternate preferred embodiment, the adaptable connection may be a permanent, but flexible connection so that the insertion rod can be bent all the way to the side. This type of flexibility would allow the insertion rod to be used to help secure the patching implant to the repair site. In particular, the adjustable connection would facilitate the insertion rod being bent over and tacked down with, for example, a stitch thereby helping to hold the patching implant in place until the patching implant grafts into place with scar and other connective tissue. One of ordinary skill in the art would appreciate that there are many suitable designs for an adaptable connection, and embodiments of the present invention are contemplated for use with any such design.

According to an embodiment of the present invention, the encephalocele repair device is comprised of one or more radiopaque markers. In the preferred embodiment, the one or more radiopaque markers are arranged on or embedded in the surface of the encephalocele patching component. In the preferred embodiment, the one or more radiopaque markers are made from a radiopaque material to be visible on x-ray and other imaging devices. Radiopaque markers may be particularly useful when the encephalocele patching component is made from a radiolucent material. In such a case, the radiopaque markers could be arranged on the encephalocele patching component so that the encephalocele patching component remains visible to x-ray and other imaging devices. The radiopaque markers may be of any suitable size and arranged in any manner as necessary to provide a complete view of the encephalocele patching component under x-ray or other imaging technology. One of ordinary skill in the art would appreciate that there are many suitable designs and arrangements for a radiopaque markers, and embodiments of the present invention are contemplated for use with any such design or arrangement.

According to an embodiment of the present invention, the encephalocele repair device is used to treat an encephalocele. In some embodiments, the encephalocele repair device may only include an encephalocele patching component, while in other embodiments the encephalocele repair device may include both an encephalocele patching component and a patching component insertion rod. The encephalocele repair device may be used to repair an encephalocele from both the inner side and outer side of the skull. When repairing an encephalocele by placing a patch the outer surface of the skull, the encephalocele repair device will typically only use the encephalocele patching component. On the other hand, when repairing an encephalocele by placing a patch the inner surface of the skull, the encephalocele repair device may use the encephalocele patching component alone or the encephalocele patching component in conjunction with the patching component insertion rod. In general, the larger the size of the encephalocele that is being repaired the larger and more rigid the encephalocele patching component of the encephalocele repair device must be in order to provide adequate support to the encephalocele. In particular, the size and rigidity of the encephalocele patching component will be largely based on the size of the encephalocele including both the diameter of the hole in the skull, as well as the mass of the encephalocele that has herniated through the hole in the skull. For example, larger holes in the skull physically require a larger and more rigid encephalocele patching component to span the hole without being overly flexed, while larger encephaloceles require a more rigid encephalocele patching component to support the mass of the encephalocele.

According to an embodiment of the present invention, the encephalocele repair device may be used to treat an encephalocele as a part of a patch on the outer surface of the skull. The outer surface repair method is typically used to repair smaller encephaloceles, as it is a typically less invasive method and smaller encephaloceles are more easily supported by an outer skull patch. In a preferred embodiment, when being used as a part of a patch on the outer surface of the skull, the encephalocele repair device will typically only include the encephalocele patching component. In the preferred embodiment, the encephalocele repair device may be used in conjunction with tissue grafts, as well as other artificial patching and packing materials to secure the encephalocele repair device in place. Those additional patching and packing materials might would be obvious to one of skill in the art. In an alternate embodiment, the encephalocele repair device may include the use of the patching component insertion rod even when the encephalocele repair device is forming a patch on the outer surface of the skull. In such an embodiment, the patching component insertion rod may be bent to the side using the adaptable connection and then stitched or otherwise secured to the skull in order to provide an additional means for securing the encephalocele patching component in place at the repair site.

According to an embodiment of the present invention, the encephalocele repair device may be used to treat an encephalocele as a part of a patch on the inner surface of the skull. The inner surface repair method is typically used to repair larger encephaloceles, as larger encephaloceles are more likely to cause an outer surface patch to fail. In some cases, an encephalocele may be repaired with a patch positioned on the inner surface of the skull, which provides an increase level of support when compared to an outer surface patch. The repair would be largely the same as the repair described above, with the encephalocele patching component of the encephalocele repair device being positioned in place with other patching and packing materials being used to secure the encephalocele repair device in place. This particular method may require a second hole, or access point, to be made in the skull so that the encephalocele repair device can be properly positioned at the repair site.

According to an embodiment of the present invention, the patching component insertion rod of the encephalocele repair device may be used to position an encephalocele patching component on the inner surface of the skull without the need for an access point being made in the skull. In a preferred embodiment, the patching component insertion for could be used to push the encephalocele patching component through the hole at the repair site, thereby pushing the encephalocele back into the skull cavity. In the preferred embodiment, the encephalocele patching component should be sufficiently flexible to bend as it is being pushed through the hole at the repair site. When the encephalocele patching component clears the edges of the hole on the inner surface of the skull, the encephalocele patching component will flex back to its original shape, allowing the encephalocele patching component to cover the hole and support the encephalocele inside of the skull. In the preferred embodiment, the encephalocele patching component should be flexible enough to be inserted through the site of the encephalocele, but rigid enough to support the encephalocele once the encephalocele patching component is positioned on the inner surface of the skull. Once the encephalocele patching component is in place, the adaptable connection may permit the patching component insertion rod to be disconnected from the encephalocele patching component with any surgical cutting tool. Alternatively, the adaptable connection could allow the patching component insertion rod to be bent to the side and tacked down with, for example, a stitch thereby helping to hold the encephalocele patching component in place until the encephalocele patching component grafts into place with scar and other connective tissue.

According to an embodiment of the present invention, the encephalocele repair device is comprised primarily of polyether ether ketone (PEEK) or a similar plastic material. In a preferred embodiment, the use of PEEK or a similar plastic allows the disk forming the encephalocele patching component to be shaped as necessary for the particular application. This is an advantage over patches made from metal or bone, which are more difficult to shape. One of ordinary skill in the art would appreciate that there are many suitable materials from which an encephalocele repair device could be made and embodiments of the present invention are contemplated for use with any such material.

Exemplary Embodiments

Turning now to FIG. 1, a perspective view of an encephalocele repair device in accordance with an embodiment of the present invention. In a preferred embodiment, the encephalocele repair device 100 is primarily comprised of an encephalocele patching component 102 and a patching component insertion rod 104. The encephalocele patching component 102 is primarily comprised of a convex front side 106 and a concave rear side (not shown).

Figure 2:
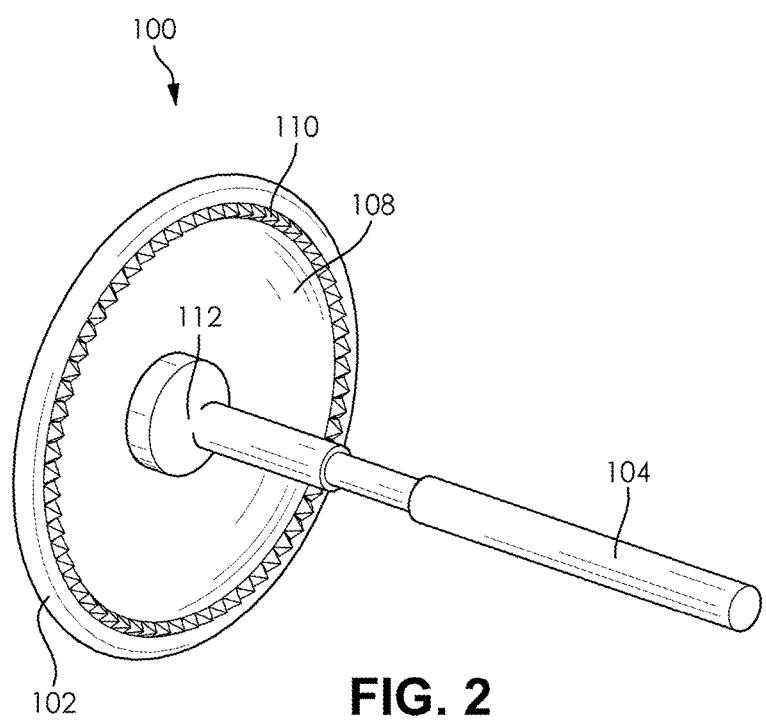
FIG. 2 is an alternate perspective view of encephalocele repair device in accordance with an embodiment of the present invention.

Turning now to FIG. 2, an alternate perspective view of an encephalocele repair device in accordance with an embodiment of the present invention. In a preferred embodiment, the encephalocele repair device 100 is primarily comprised of an encephalocele patching component 102 and a patching component insertion rod 104 extending off the concave rear side 108 of the encephalocele patching component 102. The encephalocele patching component 102 is primarily comprised of a convex front side (not shown) and a concave rear side 108. In the preferred embodiment, the concave rear side 108 may be further configured with a grafting surface area 110. The patching component insertion rod 104 connects to concave rear surface 108 via an adaptable connection 112.

Figure 3:
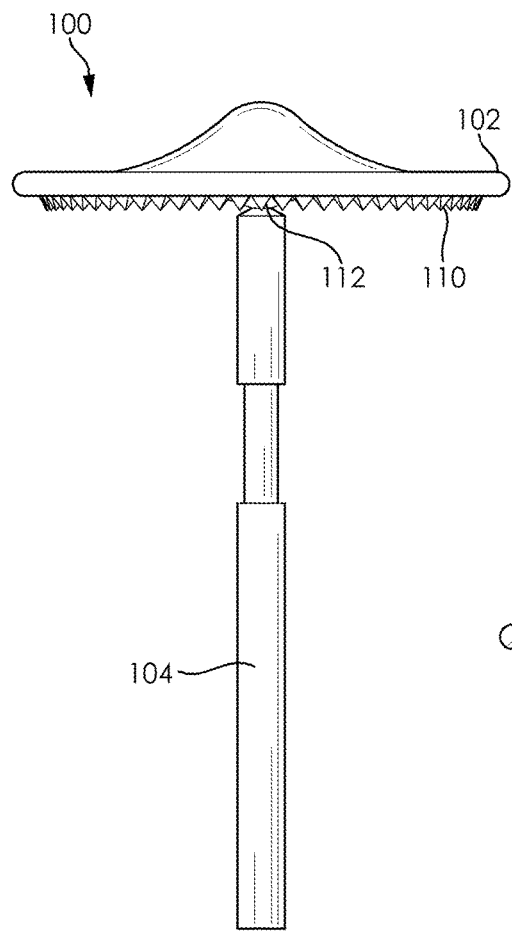
FIG. 3 is a side view of encephalocele repair device in accordance with an embodiment of the present invention.

Turning now to FIG. 3, a side view of an encephalocele repair device in accordance with an embodiment of the present invention. In a preferred embodiment, the encephalocele repair device 100 is primarily comprised of an encephalocele patching component 102 and a patching component insertion rod 104 extending off the concave rear side of the encephalocele patching component 102. In the preferred embodiment, the concave rear side may be further configured with a grafting surface area 110. The patching component insertion rod 104 connects to concave rear surface via an adaptable connection 112.

Figure 4:
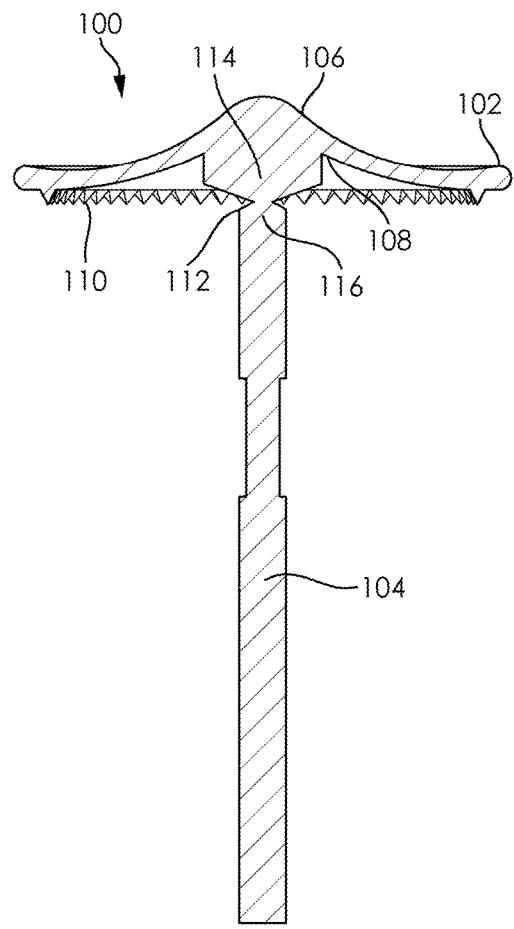
FIG. 4 is a cross-sectional view of encephalocele repair device in accordance with an embodiment of the present invention.

Turning now to FIG. 4, a cross-sectional view of an encephalocele repair device in accordance with an embodiment of the present invention. In a preferred embodiment, the encephalocele repair device 100 is primarily comprised of an encephalocele-patching component 102 and a patching component insertion rod 104 extending off the concave rear side 108 of the encephalocele patching component 102. In the preferred embodiment, the concave rear side may be further configured with a grafting surface area 110. The patching component insertion rod 104 connects to concave rear surface 108 via an adaptable connection 112. In the preferred embodiment, the adaptable rear connection 112 is comprised of a rod attachment point 114 on the concave rear side 108 of the encephalocele patching component 102 and the patching component attachment point 116 on the patching component insertion rod 104.

Figure 5:
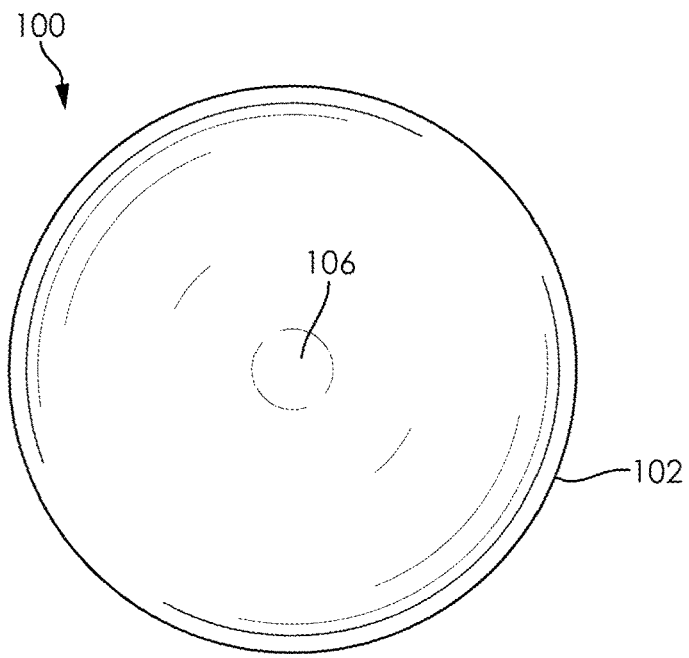
FIG. 5 is a front view of encephalocele repair device in accordance with an embodiment of the present invention.

Turning now to FIG. 5, a front view of an encephalocele repair device in accordance with an embodiment of the present invention. In a preferred embodiment, the encephalocele repair device 100 is primarily comprised of an encephalocele patching component 102 and a patching component insertion rod (not shown). The encephalocele patching component 102 is primarily comprised of a smooth convex front side 106 and a concave rear side (not shown).

Figure 6:
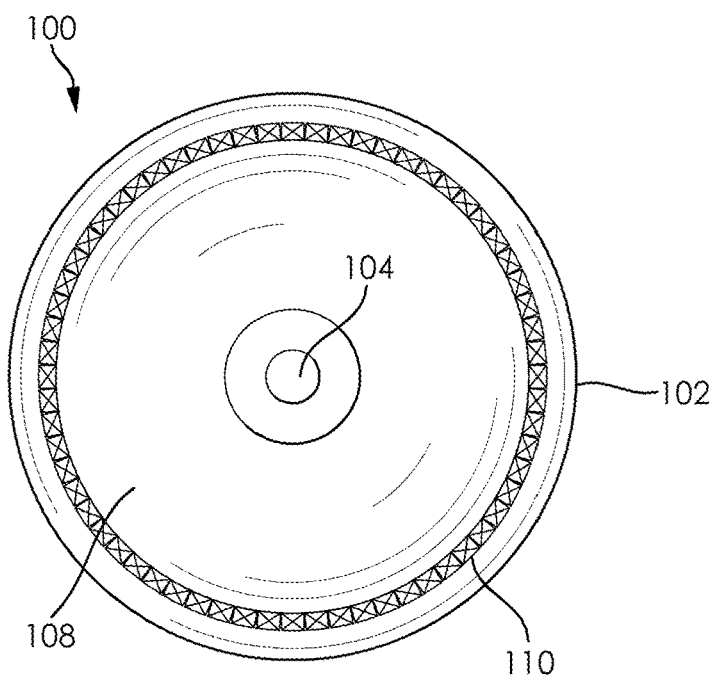
FIG. 6 is a rear view of encephalocele repair device in accordance with an embodiment of the present invention.

Turning now to FIG. 6, rear view of an encephalocele repair device in accordance with an embodiment of the present invention. In a preferred embodiment, the encephalocele repair device 100 is primarily comprised of an encephalocele patching component 102 and a patching component insertion rod 104 extending off the concave rear side 108 of the encephalocele patching component 102. The encephalocele patching component 102 is primarily comprised of a convex front side (not shown) and a concave rear side 108. In the preferred embodiment, the concave rear side 108 may be further configured with a grafting surface area 110. The patching component insertion rod 104 connects to concave rear surface 108 via an adaptable connection (not shown).

Figure 7:
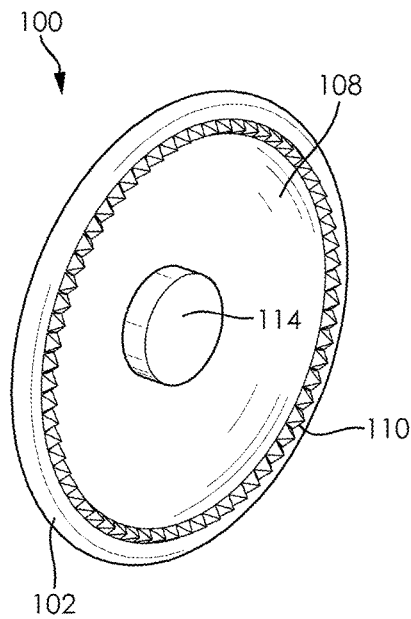
FIG. 7 is a perspective view of encephalocele repair device configured without an insertion rod in accordance with an embodiment of the present invention.

Turning now to FIG. 7, a perspective view of an encephalocele repair device without a patching component insertion rod in accordance with an embodiment of the present invention. In a preferred embodiment, the encephalocele repair device 100 is primarily comprised of an encephalocele patching component 102. The encephalocele patching component 102 is primarily comprised of a convex front side (not shown) and a concave rear side 108. In the preferred embodiment, the concave rear side 108 may be further configured with a grafting surface area 110. The concave rear side 108 may be formed with a rod attachment point 114 so that an optional patching component insertion rod can be connected to the concave rear surface 108.

Figure 8:
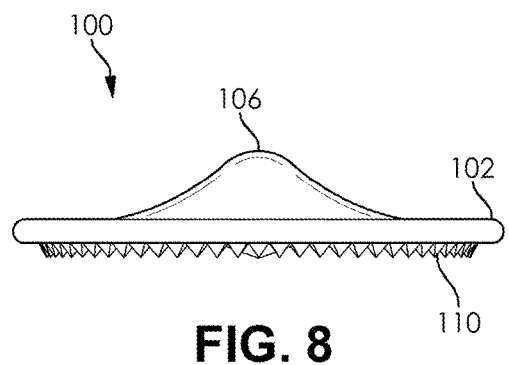
FIG. 8 is a side view of encephalocele repair device configured without an insertion rod in accordance with an embodiment of the present invention.

Turning now to FIG. 8, a side view of an encephalocele repair device without a patching component insertion rod in accordance with an embodiment of the present invention. In a preferred embodiment, the encephalocele repair device 100 is primarily comprised of an encephalocele patching component 102 with a convex front side 106 and a concave rear side (not shown). In the preferred embodiment, the concave rear side may be further configured with a grafting surface area 110.

Figure 9:
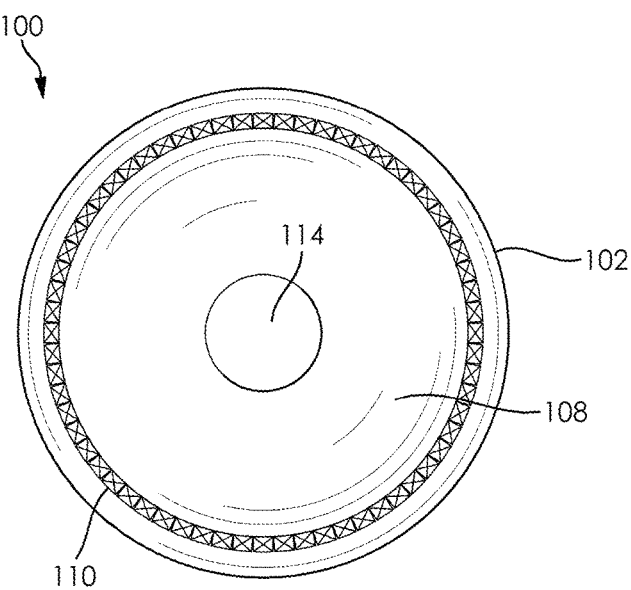
FIG. 9 is a rear view of encephalocele repair device configured without an insertion rod in accordance with an embodiment of the present invention.

Turning now to FIG. 9, a rear view of an encephalocele repair device without a patching component insertion rod in accordance with an embodiment of the present invention. In a preferred embodiment, the encephalocele repair device 100 is primarily comprised of an encephalocele patching component 102. The encephalocele patching component 102 is primarily comprised of a convex front side (not shown) and a concave rear side 108. In the preferred embodiment, the concave rear side 108 may be further configured with a grafting surface area 110. The concave rear side 108 may be formed with a rod attachment point 114 so that an optional patching component insertion rod can be connected to the concave rear surface 108.

It should be noted that the features illustrated in the drawings are not necessarily drawn to scale, and features of one embodiment may be employed with other embodiments as the skilled artisan would recognize, even if not explicitly stated herein. Descriptions of well-known components may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. An encephalocele repair device comprising:
a cap configured to function as an encephalocele patching component, said cap having a convex side, a concave side and a disk-shaped base projecting centrally from said concave side;
a straight insertion rod having a circular cross-section for its entire length, said insertion rod is connected to said base via a flexible connection,
wherein said insertion rod has a base section, a mid-section, and an end section, wherein said mid-section is interposed between said base section and said end section and has a smaller cross-sectional area than each of said base section and end section; and
a ring of knurled surface extending concentrically along a periphery of said concave side.

2. The encephalocele repair device of claim 1, wherein said cap varies in thickness between 0.5 mm and 3.5 mm.

3. The encephalocele repair device of claim 1, wherein said cap decreases in thickness from its center to its periphery.

4. The encephalocele repair device of claim 1, wherein said cap increases in thickness from its center to its periphery.

5. The encephalocele repair device of claim 1, wherein said cap has a diameter between 0.5 cm and 3.5 cm.

6. The encephalocele repair device of claim 1, further comprising one or more radiopaque markers secured to said cap.

7. The encephalocele repair device of claim 1, wherein said knurled surface is a grafting surface area, wherein said grafting surface area is adapted to promote grafting between said cap and body tissue.

8. The encephalocele repair device of claim 1, wherein the knurled surface is confined to the area along the periphery of said concave side, such that the interior of said knurled ring has a different type of surface than said knurled surface.

9. The encephalocele repair device of claim 1, wherein said knurled surface consists of a single row of teeth.

10. An encephalocele repair device comprising:
a cap configured to function as an encephalocele patching component, said cap comprising a convex side, a concave side and a disk-shaped base projecting centrally from said concave side;
a ring of knurled surface extending concentrically along a periphery of said concave side, wherein said knurled surface area is a strip of textured surface; and
an insertion rod having a circular cross-section for its entire length, said insertion rod extending from said disk-shaped base and configured to engage with and apply pressure to said cap during deployment of said cap, wherein said insertion rod has a base section adjacent to said disk-shaped base, a mid-section, and an end section, wherein said mid-section is interposed between said base section and said end section and has a smaller cross-sectional area than each of said base section and end section.

11. The encephalocele repair device of claim 10, further comprising one or more radiopaque markers secured to said cap.

12. The encephalocele repair device of claim 10, wherein the cap has a variable thickness to enable a variable flexibility across said cap.

13. An encephalocele repair device comprising:
a cap configured to function as an encephalocele patching component, said cap comprising a convex side, a concave side and a disk-shaped base projecting centrally from said concave side;
a ring of knurled surface extending concentrically along a periphery of said concave side, wherein said knurled surface area is a strip of textured surface;
an insertion rod having a circular cross-section for its entire length, said insertion rod extending from said disk-shaped base and configured to engage with and apply pressure to said cap during deployment of cap, wherein said insertion rod has a base section adjacent to said disk-shaped base, a mid-section, and an end section, wherein said mid-section is interposed between said base section and said end section and has a smaller cross-sectional area than each of said base section and end section, wherein said insertion rod is connected to said cap via an adaptable connection.

* * * * *